United States Patent [19]

Sharkany et al.

[11] Patent Number: 4,662,372
[45] Date of Patent: May 5, 1987

[54] DISPOSABLE SURGICAL INSTRUMENT AND METHOD OF FORMING

[75] Inventors: Edward J. Sharkany, Huntington; John C. O'Donnell, Stratford, both of Conn.

[73] Assignee: Acme United Corporation, Fairfield, Conn.

[21] Appl. No.: 764,404

[22] Filed: Aug. 12, 1985

[51] Int. Cl.[4] .............................. A61B 17/28
[52] U.S. Cl. .................................... 128/321
[58] Field of Search ............. 128/321, 322, 325, 346, 128/354, 340; 30/341; 81/427.5

[56] References Cited

U.S. PATENT DOCUMENTS

| | | | |
|---|---|---|---|
| 3,082,652 | 3/1963 | Marti | 81/427.5 X |
| 4,282,783 | 8/1981 | Fortune | 81/427.5 |
| 4,438,565 | 3/1984 | Hough | 30/341 |
| 4,452,106 | 6/1984 | Tartaglia | 128/354 |

FOREIGN PATENT DOCUMENTS

| | | | |
|---|---|---|---|
| 850647 | 9/1952 | Fed. Rep. of Germany | 128/321 |
| 401732 | 9/1909 | France | 128/321 |

OTHER PUBLICATIONS

American V. Mueller, Surgical Instruments Catalog, (1980), p. 405.

Primary Examiner—Michael H. Thaler
Attorney, Agent, or Firm—Mattern, Ware, Stoltz & Fressola

[57] ABSTRACT

By providing two cooperating, pivotable clamping arms, each of which incorporates an elongated, movement controlling plastic portion securely affixed to a die-cast metal or powdered metal section having a clamping face formed therein, a uniquely constructed, pivotable, jaw-clamping surgical instrument is attained. By employing die-cast metal or powdered metal sections, close tolerances and high quality is attained, while the expense of manufacture is substantially reduced. In addition, the integration of the die-cast metal or powdered metal sections with the elongated, movement controlling plastic arms achieves a trouble-free, dependable, inexpensive, disposable surgical instrument wherein the inherent advantages of both materials are optimized.

13 Claims, 7 Drawing Figures

DISPOSABLE SURGICAL INSTRUMENT AND METHOD OF FORMING

TECHNICAL FIELD

This invention relates to disposable surgical instruments, and more particularly, to pivotable, jaw-clamping type surgical instruments.

BACKGROUND ART

During the last several years, many advances have been made in efficacy and commercial viability of disposable surgical instruments, which eliminate the need for sterilization of surgical instruments after every use. Recently, however, due to the increasing expense of all surgical instruments, coupled with new accounting methods being imposed upon hospitals and other providers of medical services, the cost of disposable surgical instruments has become an increasingly important factor.

In an attempt to reduce the expense of disposable surgical instruments, while still providing a dependable and reliable product, a variety of plastic products have been developed, some with metal portions incorporated therein, where required, for added strength and rigidity. However, the attainment of a dependable, disposable, surgical, pivotable jaw-clamping instrument, which possesses close tolerances and high quality, while also being competitively priced, has eluded prior art developers.

In order to attain an effective pivotable, jaw-clamping surgical instrument, the instrument must be capable of producing and enduring large compressive forces on the faces of the jaw members and be able to withstand substantial bending forces on the arms, in order for the instrument to perform its requisite function.

In general, plastic instruments and metal reinforced plastic instruments have been totally unable to meet the demands inherent in such a product. Typically, these prior art products are incapable of having the clamping jaws fully engaged, without producing separation of a portion of the jaws when added force is applied. In addition, these prior art instruments frequency suffer breakage during use.

As a result, pivotable, jaw-clamping surgical instruments are typically made from all metal members which are either forged or formed from stainless steel. In this way, the requisite force demand to which the surgical instruments are put are capable of being attained.

Although attempts have been made to reduce the expense of manufacture for pivotable, jaw-clamping surgical instruments, no substantial cost reductions have been achieved. In this regard, some attempts have been made to employ die-casting for the construction of pivotable, jaw-clamping surgical instruments, since the expense of die-casting is substantially less than forging. However, the metals used in die casting are substantially softer, have a much lower tensile strength, and are likely to fracture more readily than forged metals. Consequently, any attempt to manufacture die-cast pivotable, jaw-clamping surgical instruments have failed, since the end product was incapable of withstanding the force demands inherent in the use of the product, without suffering unwanted bending or fracturing.

Consequently, it is a principal object of the present invention to provide a disposable, pivotable, jaw-clamping surgical instrument which incorporates die-cast jaw members and is capable of being successfully used in all surgical procedures without experiencing any degradation or failure.

Another object of the present invention is to provide pivotable, jaw-clamping, disposable surgical instruments having the characteristic features described above which are easy to employ and provide the user with a similar grip and feel as more expensive, reusable surgical instruments.

Another object of the present invention is to provide pivotable, jaw-clamping, disposable surgical instruments having the characteristic features described above which are inherently less expensive to manufacture, while still being dependable and trouble-free in use and operation.

Other and more specific objects will, in part, be obvious and will, in part, appear hereinafter.

SUMMARY OF THE INVENTION

By employing the present invention, the difficulties which have continuously plagued the prior art have been totally overcome. This unique advance in disposable surgical instruments has been achieved by constructing each of the two clamping arms of the instrument from separate materials. The jaw portion of the clamping arm of the surgical instrument is constructed from die cast metals or from powdered metals, while the arm and handle portion of each clamping arm of the surgical instrument is constructed from plastic which is securely affixed to the die-cast jaw portion. By combining the unique qualities of die-cast metals or powdered metals with the resilient flexibility of plastic, a unique, pivotable, jaw-clamping disposable surgical instrument is obtained which is capable of being manufactured at substantially reduced costs.

The only prior art systems which have attempted to combine die-cast metals with plastics have been limited to scissor-type instruments, wherein little to no jaw contact or abutting forces are experienced. In general, prior art systems have taught away from employing die-cast metals or powdered metals for jaw clamping surgical instruments, since the die-cast metals or powdered metals are softer, have much less tensile strength, and are more likely to fracture—all characteristics which pivotable, jaw-clamping surgical instruments cannot possess.

In the present invention, all of these prior art difficulties are eliminated, and a unique, disposable, pivotable, jaw-clamping surgical instrument is attained by combining die-cast metals or powdered metals with plastics in a surgical instrument which employs these particular materials so that the inherent qualities of each material is realized and optimized, while their disadvantageous qualities are minimized and virtually never become a factor. In this way, a unique construction is obtained for disposable surgical instruments which eliminates all of the prior art problems and provides a major advance in the production of high quality, low cost, pivotable, disposable, jaw-clamping surgical instruments.

The invention accordingly comprises the features of construction, combination of elements, arrangement of parts, which will be exemplified in the constructions hereinafter set forth, as well as the several steps and the relation of one or more steps with respect to each of the others in the manufacture of said instruments as exemplified in the following detailed disclosure, while the scope of the invention will be indicated in the claims.

THE DRAWINGS

For a fuller understanding of the nature and objects of the invention, reference should be had to the following detailed description taken in connection with the accompanying drawings, in which.

DETAILED DISCLOSURE

Figure 1:
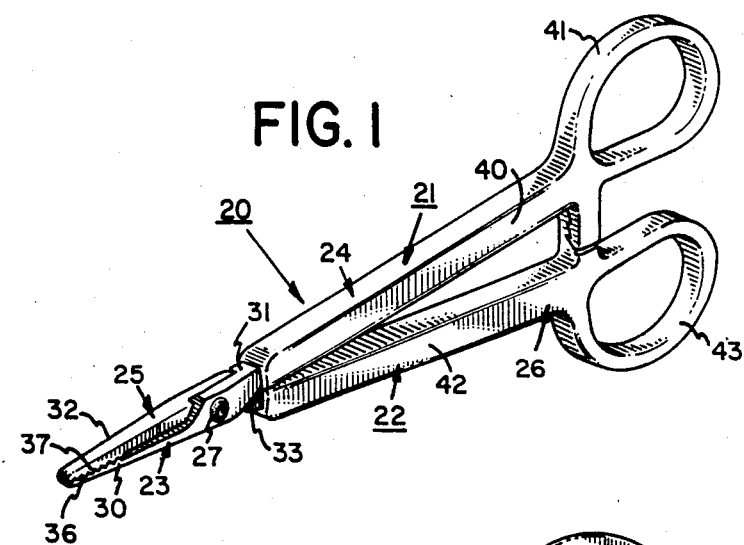
FIG. 1 is a perspective view of a typical, pivotable jaw-clamping, disposable surgical instrument embodying the teaching of the present invention.

In FIG. 1, a pivotable, jaw-clamping surgical instrument 20 embodying the present invention is shown. Surgical instrument 20 comprises two, cooperating, clamping arms 21 and 22 which are pivotally secured to each other by pivot means 27. Clamping arm 21 incorporates a metal section 23 and a plastic section 24, intimately affixed to each other, while clamping arm 22 incorporates a metal section 25 and a plastic section 26, also intimately affixed to each other.

For purposes of illustration only, and not in any limiting sense, surgical instrument 20 is depicted as a hemostat. However, as will become readily apparent from the following detailed disclosure, surgical instrument 20 of the present invention may be constructed as any type of pivotable, jaw-clamping, surgical instrument, such as a needle holder, a towel clamp, a suture clamp, a surgical staple remover, etc. Consequently, all of these alternate constructions are intended to be included as a part of the scope of the present invention.

Figure 2:
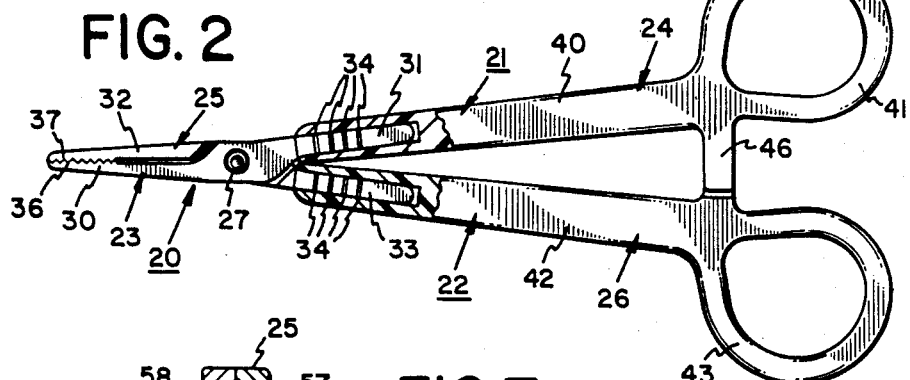
FIG. 2 is a side elevational view, partially broken away, of the surgical instrument of FIG. 1, showing the jaws in their closed position.
Figure 4:
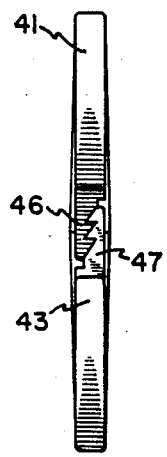
FIG. 4 is a rear elevational view of the surgical instrument of FIG. 1 showing the locking ratchet teeth of the handle portion in locked interengagement.
Figure 3:
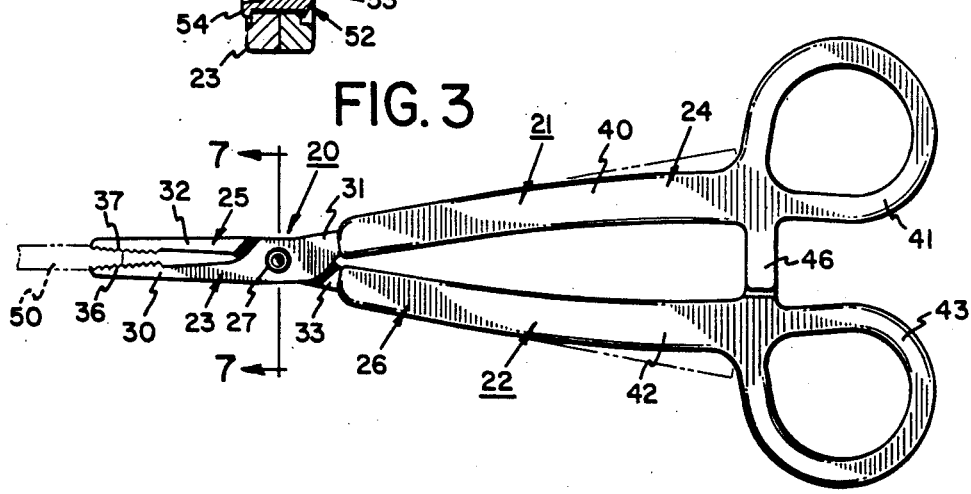
FIG. 3 is a side elevational view of the surgical instrument of FIG. 1 showing the instrument in clamped engagement with an article.
Figure 6:
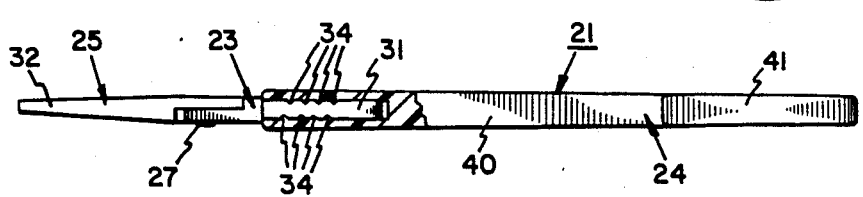
FIG. 6 is an edge view, partially broken away, of the surgical instrument of FIG. 1.

As best seen in FIGS. 2, 3 and 6, metal sections 23 and 25 are pivotally mounted to each other, preferably substantially mid way along their length. As a result, metal section 23 comprises a jaw portion 30 extending from the pivot point in one direction, and a mounting post 31 extending from the pivot point in the opposite direction. Similarly, metal section 25 comprises a jaw portion 32 extending from the pivot point in one direction, and a mounting post 33, extending from the pivot point in the opposite direction. Each metal section is angularly shaped with the jaw portion and the mounting post extending outwardly from the pivot axis to form an obtuse angle therebetween.

In addition, jaw portion 30 incorporates a serrated, clamping face 36 formed therein, while jaw portion 32 comprises a similar clamping face 37 formed therein, for cooperating, clamping interengagement with face 36 of jaw portion 30.

As mentioned above, surgical instrument 20 may be constructed for any desired purpose. As a result, clamping faces 36 and 37 are formed with the particularly desired tooth configuration or surface arrangement dictated by the particular purpose to which the surgical instrument is to be put. As a result, the conventional face constructions for needle holders, towel clamps, suture clamps, surgical staple removers, etc. would be formed as clamping faces 36 and 37 to attain the desired surgical instrument. The hemostat face construction depicted in the drawings of the present invention is shown for exemplary purposes only, and is not in any way intended to limit the present invention to any particular jaw construction or clamping face configuration.

In accordance with the present invention, metal sections 23 and 25 are formed by die casting, using conventional die-cast processes well-known in the art. In this way, metal sections 23 and 25 are formed with close tolerance details directly from the die-cast process, without requiring hand finishing or other labor intensive steps. As a result, the production costs for such components are substantially reduced. If desired, metal sections 23 and 25 may be constructed from powdered metals, using conventional techniques, with similar advantageous results.

In general, in order to form serrated, interengaging clamping faces 36 and 37, as depicted in the drawings, two separate molds must be employed for forming metal sections 23 and 25. However, by employing the present invention, labor intensive hand work on the jaw faces is eliminated, since metal sections 23 and 25 are formed with precise tooth configurations. In other surgical instruments where the clamping faces do not require tooth interengagement, such as with smooth faced needle holders, metal sections 23 and 25 comprise identical structures and, as a result, are generally formed from identical molds, thereby providing added production cost benefits.

Once metal sections 23 and 25 have been formed, the construction of clamping arms 21 and 22 are completed by securely affixing plastic sections 24 and 26 to metal sections 23 and 25. In the preferred embodiment, plastic section 24 incorporates an elongated arm 40 and an easily employable, readily accessible handle 41. Similarly, plastic section 26 incorporates an elongated arm 42 and a handle 43.

As shown in FIG. 2, elongated arm 40 of plastic section 24 is securely mounted to mounting post 31 of metal section 23. In the preferred embodiment, elongated arm 40 peripherally surrounds and lockingly engages mounting post 31 in order to achieve the desired intimate interengagement of plastic section 24 with metal section 23. As shown in FIG. 6, post 31 preferably incorporates relief zones 34 to assure secure, interengagement between plastic section 24 and metal section 23.

Similarly, elongated arm 42 of plastic section 26 is securely affixed to mounting post 33 of metal section 25 at one end thereof, by peripherally surrounding and lockingly engaging mounting post 33. In this way, secure, fixed, intimate engagement between plastic section 26 and metal section 25 is attained.

The opposed end of elongated arm 40 is secured with handle 41. In the preferred embodiment, elongated arm 40 and handle 41 are simultaneously formed of the same plastic material, thereby assuring intimate secure engagement of arm 40 with handle 41. Similarly, arm 42 and handle 43 of plastic section 26 are also preferably simultaneously formed from the identical materials, thereby assuring the secure interengagement of arm 42 with handle 43.

Although handles 41 and 43 may be formed in a variety of alternate configurations, handles 41 and 43 are preferably formed as fingerloops which are quickly and easily employed by the operator in order to controllably move clamping arms 21 and 22 relative to each other, about the pivot axis established by pivot means 27. In this way, the desired clamping interengagement of clamping faces 36 and 37 is controllably achieved by the operator quickly and easily, in order to attain the desired use of surgical instrument 20.

Figure 5:
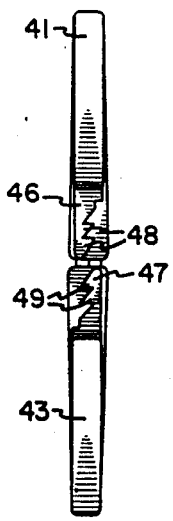
FIG. 5 is a rear elevational view of the surgical instrument of FIG. 1 showing the ratchet teeth of the handle portion in unlocked, disengagement.

In order to further enhance the usefulness of surgical instrument 20 of the present invention, handles 41 and 43 also incorporate locking fingers extending therefrom for cooperative, locking interengagement. As best seen in FIGS. 1, 3 and 5, locking finger 46 extends from handle 41, while locking finger 47 extends from handle 43.

Locking finger 46 incorporates a plurality of ramped, upstanding engaging teeth 48, while locking finger 47 incorporates similar, ramped, upstanding engaging teeth 49. With locking fingers 46 and 47 positioned for aligned, cooperating, overlying engagement, the movement of handles 41 and 43 towards each other, as shown in FIG. 5, causes fingers 46 and 47 to advance towards each other, bringing teeth 48 and 49 into camming and locking interengagement. As a result, by merely moving faces 36 and 37 into clamping engagement with a particular article, fingers 46 and 47 are brought into secure, locking interengagement, thereby automatically maintaining faces 36 and 37 in the desired clamped position. Whenever disengagement is desired, handles 41 and 43 are merely moved sideways, thereby disengaging teeth 48 and 49 from locked engagement, releasing the clamped article.

By constructing surgical instrument 20 with two, cooperating, pivotally engaged clamping arms, with each of the clamping arms incorporating a metal section and a plastic section, a surgical instrument is attained which is capable of providing secure, mating, cooperative interengagement of the entire clamping face of each clamping arm in a manner previously only attainable with expensive surgical instruments. In addition, the surgical instrument of the present invention provides trouble-free operation without fear of instrument degradation or failure during use. In order to attain these desirable, advantageous qualities, while also providing a high production, reasonably priced, precision instrument, surgical instrument 20 of the present invention has combined the advantageous qualities of a die-cast metal with the flexibility and controlled, resilient deformability of plastic material.

As briefly discussed above, die-cast metals have not been employed in jaw clamping, pivotable, disposable surgical instruments since the die-cast metal is a weak metal, as compared to steel or other forged metals. In addition, die-cast metals have comparatively low tensile strength, and thereby tend to fracture or break when exposed to a substantial bending moment or similar load. In view of these negative qualities, die-cast metals have been avoided in prior art disposable surgical instruments.

In the present invention, however, the disadvantageous characteristics of die-cast metals have been avoided by employing die casting for the formation of a section of the clamping arm. As detailed above, clamping arms 21 and 22 incorporate metal sections 23 and 25, respectively. In accordance with the teaching of the present invention, metal sections 23 and 25 comprise less than 50% of the overall length of clamping arms 21 and 22, with the remainder of clamping arms 21 and 22 comprising plastic sections 24 and 26, respectively.

As detailed above, plastic sections 24 and 26 are intimately affixed to metal sections 23 and 25, respectively, in order to form clamping arms 21 and 22. With this construction, all of the inherent advantages of die casting are realized, since metal sections 23 and 25 are capable of being mass produced, with little or no manual effort, while still incorporating precisely controlled tolerances and dimensions, including the precise construction required for clamping faces 36 and 37, to the extent that faces 36 and 37 are capable of being matingly interengaged, without necessitating labor intensive steps, such as manual dressing or deburring.

By employing the present invention, clamping arms 21 and 22 each incorporate plastic sections 24 and 26, respectively, which are securely affixed to their respective metal sections. As a result, clamping arms 21 and 22 each comprise a plastic elongated arm interposed between clamping faces 36 and 37 and handles 41 and 43 which provide controlled, resilient deformability during the use of surgical instrument 20. In this way, arm 40 of plastic section 24 and arm 42 of plastic section 26 each provides clamping arms 21 and 22 with controlled receipt and uniform distribution of the bending moment forces inherently placed upon clamping arms 21 and 22 during their use.

This is best seen in FIG. 3, where surgical clamp 20 is depicted with clamping faces 36 and 37 clampingly engaged with an article 50, with handles 41 and 43 advancing toward each other to the maximum allowable distance, causing locking finger 46 to be securely interlockingly engaged with locking finger 47. As clearly depicted in FIG. 3, both arms 40 and 42 are arcuately bent from their normal position as shown by the phantom line representing the outside surface of each arm member.

In this way, the deflection forces commonly encountered in pivotable, jaw clamping surgical instruments, which have heretofore necessitated the use of stronger metals, are completely tolerated and easily withstood by surgical instrument 20 of the present invention. Consequently, by providing a surgical instrument incorporating two clamping arms, each of which comprise a die-cast metal section intimately securely mounted to an elongated plastic section, a surgical instrument is obtained which is capable of performing all of the functions required for a surgical instrument, completely withstanding all of the loading pressures and deflection forces imposed thereon, while also being capable of being manufactured at substantially reduced costs, as compared to prior art surgical instruments.

By combining a die-cast metal section with an elongated plastic section, with the plastic section incorporating a force receiving and distributing arm which is capable of resiliently deflectively accepting and distributing load forces which would otherwise cause fractures in a die-cast metal arm, a unique, pivotable, jaw clamping, disposable surgical instrument is attained.

The construction of surgical instrument 20 of the present invention can be made with plastic sections 24 and 26 comprising a variety of sizes and shapes. However, it has been found that the most advantageous results are obtained by maintaining a substantially rectangular cross-sectional area along arms 40 and 42, while also maintaining the overall length of arms 40 and 42 equal to or greater than twice the distance from pivot means 27 to the terminating edge of mounting post 31 or 33. With this construction, arms 40 and 42 are assured to possess sufficient strength and length to receive and distribute the force load imposed thereon, and provide complete, trouble-free operation.

Figure 7:
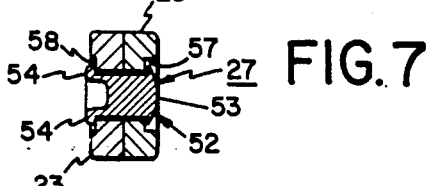
FIG. 7 is a greatly enlarged, partial, edge view of the pivot area of the surgical instrument of the present invention.

Another aspect of the present invention can best be understood by referring to FIG. 7. As depicted therein, pivot means 27 comprises, in the preferred embodiment, a rivet 52, which securely pivotally interconnects metal section 23 with metal section 25, for pivotable movement about the central axis of rivet 52.

In the preferred embodiment, rivet 52 is securely mounted to metal sections 23 and 25 in recessed zones formed in metal sections 23 and 25 to prevent any unwanted portion of rivet 52 extending beyond the outer surface of metal sections 23 and 25. In this way, surgical instrument 20 of the present invention eliminates any possibility of having a surgeon's gloves, suture material, or any other item being used during a surgical procedure, from becoming snagged or caught on rivet 52.

In the preferred embodiment, metal section 23 incorporates a recessed zone 57 into which head 53 of rivet 52 is received in its entirety. As a result, when rivet 52 is placed in its desired position, head 53 thereof is placed within recessed zone 57, thereby assuring that head 53 remains substantially co-extensive with or below the outside surface of metal section 23.

Metal section 25 also incorporates a recess zone 58 into which the rolled terminating ends 54 of rivet 52 are positioned. In this way, ends 54 of rivet 52 are maintained below the surface of metal section 25, thereby assuring that suture material, surgical gloves, or other material cannot become snagged or caught on ends 54 of rivet 52.

It will thus be seen that the objects set forth above, among those made apparent from the preceding description, are efficiently attained and, since certain changes may be made in carrying out the above method and in the construction set forth, without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described my invention, what I claim as new and desire to secure by Letters Patent is:

1. A jaw-clamping surgical instrument comprising two elongated clamping arms, pivotally mounted to each other for controlled, pivotable movement about the pivot axis defined thereby, each of said arms comprising:
   A. a unitary, integral, one-piece metal section formed by die-casting, and incorporating
      1. a jaw portion extending outwardly from said pivot axis in a first direction,
      2. a clamping face formed in the jaw portion and positioned in juxtaposed, cooperating relationship with the clamping face of said second opposed clamping arm, and
      3. a mounting post
         a. extending outwardly from said pivot axis in a second direction, and
         b. comprising a length substantially equal to the length of said jaw portion; and
   B. a plastic section incorporating
      1. an elongated arm portion comprising
         a. a first end securely affixed to the mounting post of the metal section,
         b. a second end, and
         c. an elongated, force-absorbing intermediate zone integrally connected with and extending between the first end and the second end and having a continuous length formed substantially exclusively of plastic material, said length being at least equal to the length of the mounting post of the metal section, providing said arm portion with a resiliently, axially deflectable elongated zone for receiving and withstanding bending moments imposed thereon during clamping cooperative engagement of said clamping faces of said metal sections; and
      2. a handle portion securely affixed to the second end of the elongated arm portion providing readily accessible means for controllably moving the clamping arms relative to each other;
   whereby a highly effective, mass-producible surgical instrument is obtained which is capable of meeting all operating conditions, while still being comparatively inexpensive to produce.

2. The pivotable, jaw-clamping surgical instrument defined in claim 1, wherein said metal portion comprises a substantially straight elongated member, with said jaw portion and said mounting post extending in substantially opposite directions from the pivot axis.

3. The pivotable, jaw-clamping surgical instrument defined in claim 1, wherein said metal section is further defined as comprising an angularly shaped member, with of the jaw portion and the mounting post extending outwardly from the pivot axis to form an obtuse angle therebetween.

4. The pivotable, jaw-clamping surgical instrument defined in claim 1, wherein the clamping faces of the jaw members of the two clamping arms are further defined as incorporating juxtaposed, spaced, cooperating, upstanding teeth positioned on each of said faces for cooperative interengagement and article clamping retainment therebetween.

5. The pivotable, jaw-clamping surgical instrument defined in claim 1, wherein said plastic section is further defined as comprising a single, integral arm and handle portion.

6. The pivotable, jaw-clamping surgical instrument defined in claim 1, wherein said arm portion is further defined as comprising a substantially rectangular cross-sectional area throughout substantially its entire length.

7. The pivotable, jaw-clamping surgical instrument defined in claim 1, wherein said handle portion of each clamping arm is further defined as comprising a finger loop.

8. The pivotable, jaw-clamping surgical instrument defined in claim 7, wherein the handle portion of each clamping arm is further defined as incorporating locking means extending therefrom and positioned for cooperative interlocking engagement with the locking means of the other handle portion.

9. The pivotable, jaw-clamping surgical instrument defined in claim 8, wherein said locking means is further defined as comprising a plurality of ramped, upstanding locking teeth mounted to and extending from a support plate affixed to said handle portion and positioned for camming, interlocking engagement with the locking means of the other handle portion.

10. The pivotable jaw-clamping surgical instrument defined in claim 1, wherein said pivot means is further defined as comprising a rivet and said metal sections are further defined as incorporating recessed zones directly adjacent said rivet for receiving the head of the rivet in the recessed zone of one metal section and the terminating end of the rivet within said recess zone of the other metal section, thereby providing a substantially smooth outer peripheral surface about the rivet area with the rivet having no portion thereof extending beyond the surface of the metal sections, whereby any possibility of snagging or catching material on said rivet is eliminated.

11. A method for forming a pivotable jaw-clamping surgical instrument comprising the steps of:
 A. die-casting a first metal section incorporating a first mounting post and a first jaw portion having a clamping face formed therein;
 B. die casting a second metal section incorporating a second mounting post and a second jaw portion having a clamping face formed therein, constructed for cooperative clamping interengagement with the clamping face of said first metal section;
 C. forming a first plastic section incorporating an elongated force absorbing arm portion and a handle portion, said arm portion having first and second ends and being composed substantially exclusively of plastic material and being formed with a length at least equal to the length of said first mounting post, the handle portion of the arm portion thereof being securely affixed to said second end of the arm portion;
 D. forming a second plastic section incorporating an elongated force absorbing arm portion and a handle portion, said arm portion having first and second ends and being composed substantially exclusively of plastic material and being formed with a length at least equal to the length of said second mounting post, the handle portion thereof securely affixed to said second end of the arm portion;
 E. forming a first clamping arm by securely affixing said first end of the elongated force absorbing arm portion of the first plastic section to the first mounting post of the first metal section,
 F. forming a second clamping arm by securely affixing said first end of the elongated force absorbing arm portion of the second plastic section to the second mounting post of the second metal section,
 G. positioning said first clamping arm in cooperating, aligned engagement with said second clamping arm, with portions of the metal section being in overlying mating engagement; and
 H. riveting the first clamping arm to the second clamping arm to provide a pivotable, jaw-clamping surgical instrument wherein said clamping faces of the jaw portions are easily moved into and out of mating clamping interengagement by said handle portion of the plastic section.

12. The process defined in claim 11, wherein said riveting step is performed substantially mid way along the length of the metal sections, thereby forming metal sections with the jaw portion thereof substantially equal in length to the length of said mounting post.

13. The method defined in claim 12, wherein the arm portions of said plastic sections are each further defined as being constructed with an overall length equal to at least twice the length of the mounting post of the metal section to which the arm portion is secured.

* * * * *